United States Patent [19]

Polyak

[11] Patent Number: 4,878,889
[45] Date of Patent: Nov. 7, 1989

[54] ARTIFICIAL SPHINCTER DEVICE
[75] Inventor: Mark Polyak, Minneapolis, Minn.
[73] Assignee: American Medical Systems, Inc., Minnetonka, Minn.
[21] Appl. No.: 211,346
[22] Filed: Jun. 24, 1988
[51] Int. Cl.$^4$ .............................................. A61F 1/00
[52] U.S. Cl. .............................. 600/31; 128/DIG. 25; 623/14
[58] Field of Search ....................... 128/346, DIG. 25; 600/29-31; 623/14

[56] References Cited

U.S. PATENT DOCUMENTS

| | | | |
|---|---|---|---|
| Re. 31,121 | 1/1983 | Reinicke | 137/493 |
| 3,750,194 | 8/1973 | Summers | 3/1 |
| 3,854,469 | 12/1974 | Giori et al. | 600/31 |
| 4,167,952 | 9/1979 | Reinicke | 137/493 |
| 4,197,835 | 4/1980 | Reinicke | 128/1 |
| 4,222,377 | 9/1980 | Burton | 128/1 |
| 4,256,093 | 3/1981 | Helms et al. | 128/1 |
| 4,386,601 | 6/1983 | Trick | 128/1 |
| 4,412,530 | 11/1983 | Burton | 128/1 |
| 4,417,567 | 11/1983 | Trick | 128/1 |
| 4,549,531 | 10/1985 | Trick | 128/1 |

*Primary Examiner*—Dalton L. Truluck
*Attorney, Agent, or Firm*—Peter C. Richardson; Lawrence C. Akers; Michael J. Pantuliano

[57] ABSTRACT

Disclosed is an apparatus for controlling the discharge of materials through a body passage. The invention comprises a fluid actuated artificial sphincter mechanism that surrounds the body passage. The artificial sphincter includes an inflatable cuff surrounded by a hollow resilient C-shaped reservoir ring. The cuff, ring and pump are in fluid communication with each other. The fluid communication between the cuff and reservoir ring is controlled by a flow resistor means. In operation, the pump draws fluid from the cuff and diverts the fluid into a reservoir ring. By pumping the fluid from the cuff, the cuff deflates opening the body passage. Pumping the fluid into the reservoir ring increases the pressure in the ring causing the ring to open. As the ring opens the ring allows the cuff to move further away from the body passage opening the body passage further. The fluid displaced in the ring is continuously diverted from the reservoir ring back to the cuff. A flow resistor controls the flow rate of fluid back into the cuff. The resistor allows the cuff to gradually re-inflate to again occlude flow through the body passage.

11 Claims, 2 Drawing Sheets

ARTIFICIAL SPHINCTER DEVICE

BACKGROUND OF THE INVENTION

1. Field of the Invention

This invention relates to a device for occluding a body passage. More particularly, this invention relates to a device for controlling flow of fluids through a body passage acting much like a sphincter.

2. Brief Description of the Prior Art

Incontinence is the inability to voluntarily control the discharge of excretory materials. The condition may be caused by physical, neurological or psychological traumas. Incontinence is a major medical problem that affects several million Americans of all ages. This condition is the source of public stigma, often forcing those affected to withdraw from regular social activities.

Recently, surgical processes and devices have been developed to address and treat incontinence. Many of the surgical processes employ devices that occlude the affected body passage. Inflatable fluid actuated artificial sphincters are one type of such known devices for occluding body passages, especially the urethra.

Artificial sphincters now available include an inflatable cuff configured to surround and occlude the body passage, a pump and a bulb type reservoir. There are two types of reservoir bulbs available—a nonexpandable pressure variable bulb and an expandable constant pressure type bulb. The basic components are connected by fluid transmission lines. One conduit or fluid transmission line connects the cuff with the pump. A second conduit or fluid transmission line connects the pump with the reservoir bulb.

The cuff is inflated to occlude the body passage and deflated to allow the discharge of fluid through the body passage. The cuff is maintained in a normally inflated (closed) position.

The presently available fluid actuated artificial spincters have proven to be effective. However, there are some problems associated with present systems. For instance, the components of presently available devices are separately implanted.

The reservoir bulbs now used are implanted in separate area away from the cuff and other components. Separate implantation increases the time required to surgically implant the device. Consequently, it would be desirable to remove the need to separately implant the reservoir bulb.

The presence of any implant can cause irritation to the surrounding tissue. Increasing the number of components separately implanted will effect more tissue. Irritated tissue must adapt to the implanted components before the sphincter should be activated. Otherwise, the body may reject the implant, or worse cause infection.

In some cases, even though the surrounding tissue is allowed to adapt, the expansion and contraction of the constant pressure reservoir bulbs will cause erosion and scarring. Consequently, it is desirable to reduce the number and size of the components implanted.

The problems discussed are not meant to be exhaustive of the problems associated with the present device. Rather, the problems disclosed are meant to be illustrative of potential areas of improvement.

SUMMARY OF THE INVENTION

The present invention addresses the problems associated with fluid controlled, artificial sphincter systems having bulb type reservoirs. The invention is especially helpful in reducing the trauma caused by separately implanted reservoir bulbs.

Briefly, one embodiment of the invention comprises a fluid actuated artificial sphincter having an inflatable cuff in direct contact with a body passage, a hollow resilient C-shaped reservoir ring that surrounds the cuff and a means for inflating ("pump") the cuff. The cuff, ring and pump are al in fluid communication with each other.

A first fluid transmission line is connected at one end to the suction end of the pump and at the other to the cuff to provide fluid communication between the cuff and pump. The first fluid transmission line includes a one-way valve. The valve is oriented to allow flow from the cuff to the suction end of the pump only.

A second fluid transmission line is connected at one end to the discharge end of the pump and at the other to the reservoir ring to provide fluid communication between the pump and reservoir ring. The second fluid transmission line also includes a one-way valve. The valve is oriented to allow flow of fluid from the discharge end of the pump to the reservoir ring only.

A third fluid transmission line is connected between the first and second fluid transmission lines. The third fluid transmission line is connected at one end to the first fluid transmission line between the cuff and the first one-way valve. The other end is connected to the second fluid transmission line between the reservoir ring and the second one-way valve. The third fluid transmission line includes a one-way flow resistor. The flow resistor is oriented to allow continuous regulated flow from the reservoir ring back into the cuff until the pressure of the fluid in the reservoir is unable to overcome the resistance of the flow resistor.

The present invention possesses several features and advantages not possessed by artificial sphincters having bulb type reservoirs. The resilient reservoir ring is the component responsible for many of the advantages.

The reservoir ring surrounds and attaches to the cuff. This feature allows both components to be implanted as one unit reducing the time required to surgically implant the device. Also, less tissue is affected because the reservoir is not implanted into a separate area of tissue.

The reservoir ring of the present invention is smaller than the reservoir bulb. This feature again makes the invention easier to implant. It also reduces the chance and amount of trauma to tissue surrounding the implant caused by the larger bulb type reservoirs.

The reservoir ring of the present invention is resilient and does not expand to the extent that the constant pressure type reservoir bulbs do. This feature reduces the chance and amount of scaring and erosion to tissue surrounding the implant.

A second preferred embodiment comprises the inflatable cuff surrounded by the reservoir ring and a motion control ring that surrounds the reservoir ring. The second embodiment includes the motion control rings as the means for inflating the cuff rather than a pump.

The cuff and reservoir ring are in fluid communication with each other. A fluid transmission line provides the fluid communication.

The motion control ring is hollow, resilient and C-shaped. A heating circuit and a fluid are disposed within the motion control ring.

The second preferred embodiment includes an additional feature and advantage over presently available artificial sphincters. All three major components are constructed as a unit. This feature allows the artificial sphincter to be implanted as a single unit. This feature also reduces the amount of tissue that will be subjected to the implant.

The enumerated features are not meant to be exhaustive. Rather they are meant to show how the present invention addresses some of the problems now associated with artificial sphincters having bulb-type reservoirs.

DETAILED DESCRIPTION OF THE DRAWINGS

Figure 1:
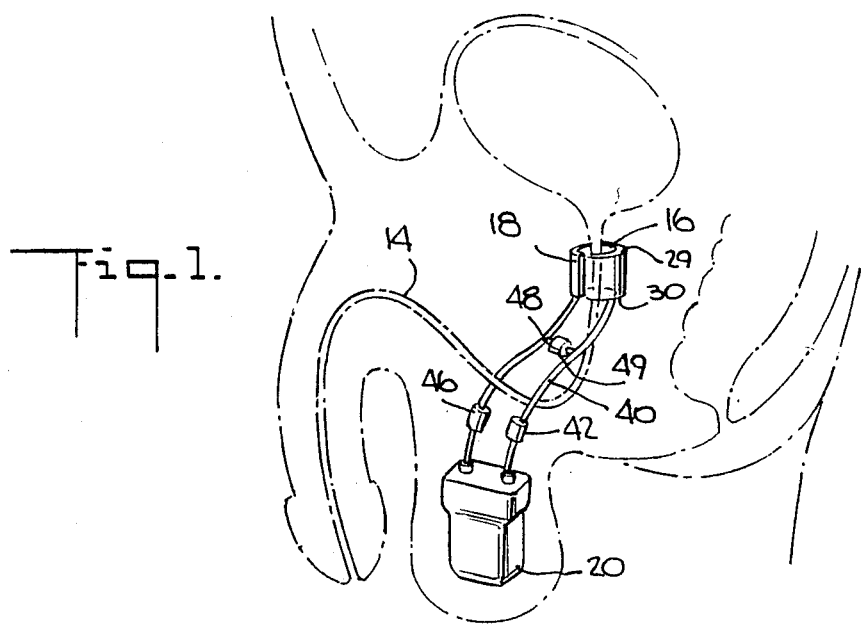
FIG. 1 is an environmental view illustrating an artificial sphincter of the first preferred embodiment of the present invention.
Figure 2:
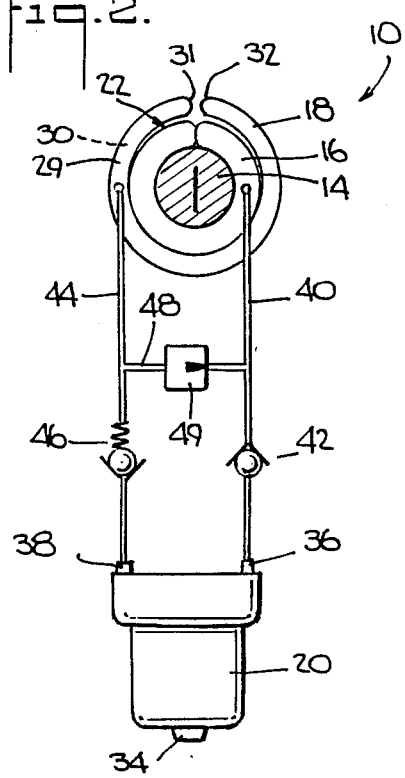
FIG. 2 schematically illustrates the artificial sphincter of the first preferred embodiment in its normally closed position.
Figure 3:
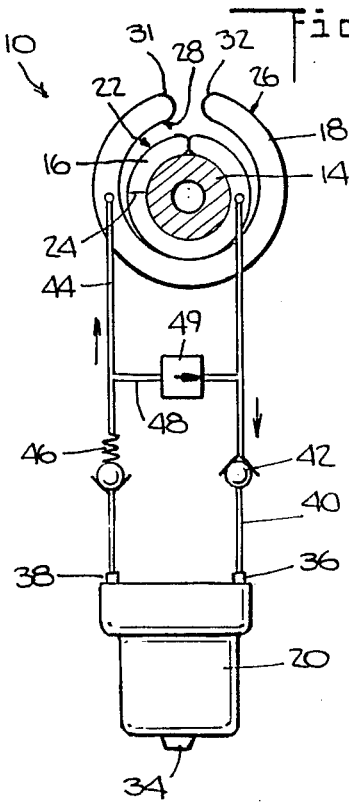
FIG. 3 schematically illustrates the artificial sphincter of the first preferred embodiment in its open position.

Illustrated in FIGS. 1-3 is a fluid actuated artificial sphincter 10 implanted in a human body 12. The artificial sphincter 10 surrounds and is capable of occluding a body passage 14. The artificial sphincter 10 includes a cuff 16, a reservoir ring 18 and a pump (means for inflating and deflating the cuff) 20.

The cuff 16 surrounds the body passage 14 being occluded. The cuff 16 is inflatable having a generally non-elastic backing 22 with a flexible inner expanding skin 24. The cuff 16 is held in a normally inflated position where the inflatable skin 24 is in direct contact with the body passage 14.

The reservoir ring 18 surrounds cuff 16. The ring 18 is hollow, resilient and C-shaped. FIG. 2 illustrates the ring 18 in its unstressed memory shape. The ring 18 has an outer face 26, an inner face 28, sides 29 and 30 and ends 31 and 32. The ring's inner face 28 is preferably attached to the cuff's backing 24. The reservoir ring 18 and cuff 16 are implanted around the affected body passage as one unit.

Preferably the pump 20 includes a septum 34, a suction end 36 and a discharge end 38. The pump 20 is in separate one-way fluid communication with the cuff 16 and the ring 18. The pump 20 is separately implanted in the body 12. Preferably the implanted pump 20 is situated in the body 12 to allow external actuation of the pump 20.

The pump's suction end 36 is in direct fluid communication with the cuff 16 through a first fluid transmission line 40. As shown in FIG. 2, the first fluid transmission line 40 includes a first one-way valve 42. The valve 42 is oriented to allow flow of the fluid from the cuff 16 to the pump 20 only.

The pump's discharge end 38 is in fluid communication with the reservoir ring 18 through a second fluid transmission line 44. The second fluid transmission line 44 includes a second one-way valve 46. The valve 46 is oriented to allow flow of the fluid from the discharge end 38 of the pump to the reservoir ring 18 only.

Shown in FIGS. 2 and 3, the first fluid transmission line 40 and the second fluid transmission line 44 are in direct fluid communication with each other through a third fluid transmission line 48. The third fluid transmission line 48 is connected at one end to the first fluid communication line 40 between the cuff 16 and the first one-way valve 42. The other end of the third fluid transmission line 48 is connected to the second fluid transmission line 44 between the reservoir ring 18 and the second one-way valve 46.

Alternatively, the third fluid transmission line 48 may be directly attached at one end to the cuff 16 and at the other end to the reservoir ring 18.

A flow resistor 49 is disposed in the third fluid transmission line 48. The flow resistor 49 is oriented to allow flow from the reservoir ring 18 to the cuff 16 only.

Operation of the first preferred embodiment of the present invention is shown in FIGS. 2 and 3.

FIG. 2 shows the artificial sphincter 10 in its normally closed position. In this position the cuff 16 is inflated to occlude the body passage 14. The reservoir ring 18 also applies pressure to the cuff 16 to hold the body passage 14 closed.

FIG. 3 shows the artificial sphincter 10 in the open position. To open the body passage 14, the cuff 16 must be deflated. To deflate the cuff 16, the operator must actuate the pump 20.

Actuating the pump 20 causes fluid to be drawn from the cuff 16 through the first transmission line 22 into the suction end 36 of the pump 20. The fluid is then transferred through the pump 20 out its discharge end 38 through the second transmission line 44 and into the reservoir ring 18. Pumping fluid into the reservoir ring 18 increases the pressure of the fluid in the reservoir ring 18. The increased fluid pressure will cause the resilient reservoir ring 18 to attempt to straighten out where the ends 31 and 32 separate. As the ring 18 attempts to straighten out, the cuff 16, attached to the ring 18, is drawn further away from the body passage 14 to open the passage 14 even further.

To reclose the body passage 14, the cuff 16 must be reinflated. The cuff 16 is automatically and continuously reinflated through the third fluid transmission line 48. The flow resistor 49 regulates the flow rate of fluid from the reservoir ring 18 to the cuff 16. The flow from the ring 18 to the cuff 16 continues until the pressure of the fluid in the reservoir 18 is insufficient to overcome the resistance of the flow resistor 49.

Figure 4:
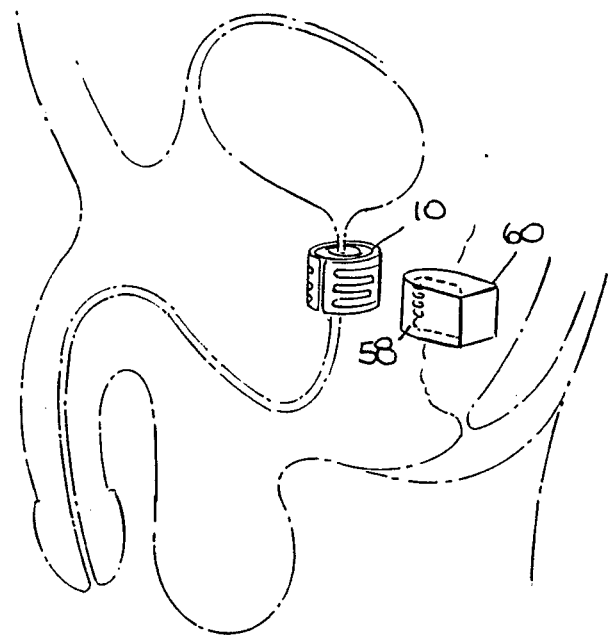
FIG. 4 is an environmental view illustrating the artificial sphincters of the second preferred embodiment of the present invention.
Figure 5:
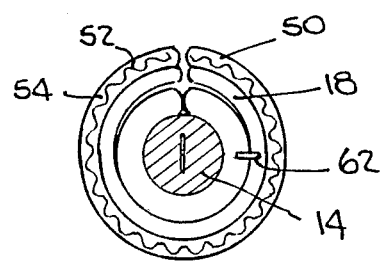
FIG. 5 illustrates the second preferred embodiment of the present invention in its normally closed position.
Figure 6:
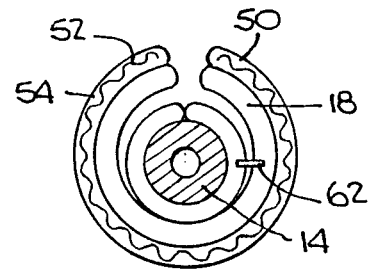
FIG. 6 illustrates the second preferred embodiment of the present invention in its open position.

Shown in FIG. 4-6 is a second preferred embodiment of the present invention. This fluid actuated artificial sphincter 10 includes the cuff 16, the reservoir ring 18 that surrounds the cuff 16 and a motion ring 50 that surrounds the reservoir ring 18. The cuff 16 is identical in both embodiments.

The resilient reservoir ring 18 is essentially identical in both embodiments except its unstressed memory shape is different. In the second embodiment the memory shape of the reservoir ring 18 is shown in FIG. 5. In its preferred memory shape, the ring 18 is in an expanded position where the ends 31 and 32 are separated.

The motion control ring 50 takes the place of the pump as the means for inflating and deflating the cuff 16. The motion control ring 50 is hollow, C-shaped and resilient. The memory shape of the motion control ring 50 is shown in FIG. 5.

A heating circuit 52 and a separate fluid 54 are disposed within the motion control ring 50. Preferably, the fluid 54 has a low boiling point yet higher than the body temperature of the subject into which the device is implanted.

The heating circuit 52 preferably includes a resistive heating element and a coil 58. An electric power source 60, external to the body 12 induces a heat generating current into the heating circuit 52 through the coil 58. Alternatively, the heating circuit 52 may include a resistive element 56 and a remotely actuated power source 60 (e.g., batteries) implanted inside the body.

The cuff 16 and the reservoir ring 18 are in fluid communication through a first fluid communication line 62. There is no fluid communication between the motion control ring 50 and either the cuff 16 or the reservoir ring 18.

Operation of the second preferred embodiment is shown in FIGS. 5 and 6. FIG. 5 shows the second preferred embodiment in its normally closed position. In the normally closed position the cuff 16 is inflated to occlude the body passage 14; and the reservoir ring 18 is compressed by the motion control ring 50 where the ends 31 and 32 are pushed together. The compressed reservoir ring 18 also aids in occluding the body passage 14.

FIG. 6 shows the second preferred embodiment in the open position. To open the body passage 14, the cuff 16 must be deflated. To deflate the cuff 16, the heating circuit 52 is activated. The circuit 52 is activated by either remotely activating the power source 60 or inducing current into the circuit 52 through the external power source 60 and coil 58. Once the circuit 52 is activated, the current carried through the heating element 56 heats the fluid 54. The heated fluid 54 expands and increases the pressure in the motion control ring 50.

Increasing the pressure in the control ring 50 causes the control ring 50 to attempt to straighten out and open. As the control ring 50 opens, the reservoir ring 18 also opens seeking its memory shape. As the reservoir ring 18 opens, the volume inside the ring 18 increases drawing fluid away from the cuff 16.

The inside volume of the reservoir ring 18 increases, decreasing the internal pressure. As the pressure on the ring 18 decreases, the fluid in the cuff 16 flows through the first fluid transmission line 62 into the reservoir ring 18. This process deflates the cuff 16, opening the body passage 14.

The artificial sphincter 10 will remain open until the heating circuit 52 is deactivated. Deactivating the heating circuit allows the fluid 54 to cool. As the fluid 54 cools, the motion control ring 50 closes, seeking its resilient memory shape. As the control ring 50 closes, it compresses the reservoir ring 18 decreasing the volume inside the ring 18.

Decreasing the available volume in the ring 18 causes fluid 11 to flow from the reservoir ring 18 into the cuff 16. This process reinflates the cuff 16 and again occludes the body passage 14.

Preferred principles, embodiments and modes of operation have been described in this specification. However, the invention is not to be construed to be limited to the particular forms disclosed because they are regarded as illustrative rather then restrictive. Furthermore, variations and changes may be made by those skilled in the art without departing from the spirit of the invention.

What is claimed is:

1. An implantable, unitary artificial sphincter for a body passage comprising:
    a. an inflatable, flexible cuff adapted to be positioned around the body passage, which when inflated closes around and shuts the body passage, and when deflated opens the body passage;
    b. an inflatable, flexible reservoir ring disposed around and fastened to the cuff, and predisposed upon inflation to straighten and open outward from the body passage;
    c. a fluid passageway interconnecting the cuff and the ring; and
    d. means for transferring fluid from the cuff to the reservoir ring.

2. An artificial sphincter for a body passage comprising:
    a. an inflatable cuff adapted to be disposed around a body passage;
    b. a hollow C-shaped reservoir ring adapted to be disposed around the inflatable cuff;
    c. a pump having a suction connection and a discharge connection;
    d. a first fluid conduit transmission line connecting the pump suction with the inflatable cuff;
    e. a second fluid transmission line connecting the pump discharge with the hollow containment ring;
    f. a first one-way flow controller for controlling the flow of fluid through the first fluid transmission line from the inflatable cuff to the pump;
    g. a second one-way flow controller for controlling the flow of fluid through the second fluid transmission line from the pump to the reservoir ring;
    h. a third fluid transmission line connected at one end to the first fluid transmission line between the first one-way flow controller and the inflatable cuff and at the other end to the second fluid communication line between the second one-way flow controller and the reservoir ring; and
    i. a means for controlling the flow rate through the third fluid transmission line.

3. An artificial sphincter according to claim 2 where the third fluid transmission line is connected at one end to the inflatable cuff and at the other end to the reservoir ring.

4. An artificial sphincter according to claim 3 where the pump further includes a septum.

5. An artificial sphincter according to claim 2 where the first means for controlling the flow of fluid and the second means for controlling the flow of fluid each comprise a one-way check valve.

6. An artificial sphincter according to claim 2 where the means for regulating the flow rate through the third fluid transmission line includes a one-way flow resistor oriented to allow flow of fluid from the reservoir ring to the cuff only.

7. An artificial sphincter comprising:
    a. an inflatable cuff adapted to be disposed around a body passage;
    b. a hollow C-shaped reservoir ring adapted to be disposed around and in fluid communication with the cuff;
    c. a hollow C-shaped motion control ring adapted to be disposed around the reservoir ring and to be filled with a fluid; and
    d. a heating means disposed within the motion control ring.

8. An artificial sphincter according to claim 7 where the inflatable cuff is attached to the reservoir ring.

9. An artificial sphincter according to claim 7 where the reservoir ring is attached to the motion control ring.

10. An artificial sphincter according to claim 7 where the heating means includes a heating circuit comprising:
   a. a resistive heating element; and
   b. a remotely actuated power source.

11. An artificial sphincter according to claim 7 where the heating means includes a heating circuit comprising:
   a. a resistive heating element;
   b. an inductor; and
   c. an external electric power source for inducing electric power into the inductor.

* * * * *